US010188549B2

(12) United States Patent
Young

(10) Patent No.: US 10,188,549 B2
(45) Date of Patent: Jan. 29, 2019

(54) EXOTHERMIC THERAPEUTIC NATURAL MASSAGE SHELLS

(75) Inventor: Daniel Young, Henderson, NV (US)

(73) Assignee: FOREVER YOUNG INTERNATIONAL, INC., Las Vegas, NV (US)

( * ) Notice: Subject to any disclaimer, the term of this patent is extended or adjusted under 35 U.S.C. 154(b) by 975 days.

(21) Appl. No.: 13/508,522

(22) PCT Filed: Nov. 4, 2010

(86) PCT No.: PCT/US2010/055376
§ 371 (c)(1),
(2), (4) Date: Jun. 29, 2012

(87) PCT Pub. No.: WO2011/056922
PCT Pub. Date: May 12, 2011

(65) Prior Publication Data
US 2012/0265108 A1 Oct. 18, 2012

Related U.S. Application Data

(60) Provisional application No. 61/259,041, filed on Nov. 6, 2009.

(51) Int. Cl.
A61F 7/03 (2006.01)
A61H 7/00 (2006.01)
(Continued)

(52) U.S. Cl.
CPC ............ A61F 7/03 (2013.01); A61H 7/003 (2013.01); A61H 15/0092 (2013.01);
(Continued)

(58) Field of Classification Search
CPC ........... A61F 7/03; A61F 7/003; A61H 7/003; A61H 15/0092; A61H 2201/0278
(Continued)

(56) References Cited

U.S. PATENT DOCUMENTS 1,380,986 A * 6/1921 Olov ................ A61H 7/003
215/382
4,060,932 A 12/1977 Leto et al.
(Continued)

FOREIGN PATENT DOCUMENTS

CH 275963 A 6/1951
WO 9959508 A1 11/1999

OTHER PUBLICATIONS

International Bureau, International Search Report for International Application No. PCT/US2010/055376, dated May 12, 2011, pp. 1-2, Geneva, Switzerland.
(Continued)

Primary Examiner — Timothy Stanis
(74) Attorney, Agent, or Firm — Troutman Sanders LLP

(57) ABSTRACT

An exothermic natural massage shell includes a natural bivalve shell comprising a first half and a second half adhered together with an adhesive to form a hollow chamber. An aperture is formed in the first half to provide a portal to the hollow chamber of the bivalve shell. A reactant is disposed inside the hollow chamber of the bivalve shell. The reactant may be a reactive powder mixture disposed inside a fluid-permeable pouch. Combining the reactant with an activator inside the hollow chamber of the bivalve shell causes an exothermic reaction that heats the bivalve shell and maintains the bivalve shell at a substantially constant elevated temperature for a duration of time. The adhesive adhering the first shell half to the second shell half includes a first elastomeric polymer bonding agent with balanced coefficient of expansion properties and a second flexible resin sealant that makes the adhesive moisture-proof.

14 Claims, 3 Drawing Sheets

(51) Int. Cl.
   *A61H 15/00* (2006.01)
   *A61F 7/02* (2006.01)
(52) U.S. Cl.
   CPC .............. *A61F 2007/0203* (2013.01); *A61F 2007/0258* (2013.01); *A61H 2015/0014* (2013.01); *A61H 2201/0278* (2013.01)
(58) Field of Classification Search
   USPC ..................... 601/15–16, 135, 137, DIG. 1
   See application file for complete search history.

(56) References Cited

U.S. PATENT DOCUMENTS

| | | | | |
|---|---|---|---|---|
| 4,169,822 A | * | 10/1979 | Kutch et al. | ............... 523/450 |
| 4,366,804 A | * | 1/1983 | Abe | ............... 126/263.02 |
| 4,462,224 A | * | 7/1984 | Dunshee et al. | ............... 62/530 |
| 4,844,072 A | * | 7/1989 | French et al. | ............... 607/104 |
| 4,884,560 A | * | 12/1989 | Kuracina | ............... 601/19 |
| 5,443,056 A | | 8/1995 | Smith et al. | |
| 6,341,602 B1 | * | 1/2002 | Fulcher | ............... 126/263.07 |
| 2003/0080158 A1 | | 5/2003 | Cull | |
| 2003/0163087 A1 | | 8/2003 | Noice et al. | |
| 2006/0258962 A1 | | 11/2006 | Kopanic et al. | |
| 2007/0032751 A1 | | 2/2007 | Roman | |
| 2013/0047974 A1 | * | 2/2013 | Payen et al. | ............... 126/263.07 |

OTHER PUBLICATIONS

International Bureau, International Preliminary Report on Patentability Chapter I for International Application No. PCT/US2010/055376, dated May 8, 2012, pp. 1-6, Geneva, Switzerland.

International Bureau, Written Opinion of the International Search Authority for International Application No. PCT/US2010/055376, dated May 6, 2012, pp. 1-5, Geneva, Switzerland.

* cited by examiner

EXOTHERMIC THERAPEUTIC NATURAL MASSAGE SHELLS

CROSS-REFERENCE TO RELATED APPLICATIONS

This application is a United States national stage entry of International Application No. PCT/US2010/055376 filed Nov. 4, 2010, which claims priority to U.S. provisional patent application Ser. No. 61/259,041 filed Nov. 6, 2009, entitled "Exothermic Therapeutic Natural Massage Shells," the contents of which are incorporated herein by reference as if set forth verbatim.

FIELD

The embodiments disclosed herein relate generally to therapeutic treatments, and more particularly to natural shells used for massages.

BACKGROUND

A popular therapeutic massage technique involves heating natural stones or ceramic implements and using them to massage different parts of the body of the massage recipient. Typically the massage implements are heated with an external heat source such as a container of hot water or an electric heater. However, this approach has several drawbacks. First, the massage therapist must take care to not overheat the implements and burn the massage recipient, but at the same time ensure that the implements are hot enough to achieve their therapeutic purpose. Second, the implements begin cooling the moment they are removed from the external heat source. Even if the implements are at the desired temperature when they are first used, the implements constantly cool down until they must be returned to the external heat source. Thus, much of the time and effort of the massage therapist is occupied by shuttling implements between the heat source and the massage recipient, rather than being completely focused on performing the massage.

Another therapeutic massage technique involves using natural sea shells, particularly bivalve shells. However, using natural shells to perform a massage suffers from the same drawbacks mentioned above with respect to other heated massage implements. Additionally, natural bivalve shells present another problem, namely that the two halves of the bivalve shell must be adhered together. However, the massage shells undergo repeated heating and cooling cycles over their lifetimes as the massage therapist heats the shells for the massage and allows them to cool after the massage is complete. During each heating and cooling cycle, the shells expand and contract a small amount. Over time, this minute cyclical change in size causes the adhesive holding the two halves together to fail so that the two valves break apart.

Accordingly, it would advantageous to provide a massage implement that remains at a desired elevated temperature for a relatively long period of time, preferably for the duration of a typical massage. Additionally, it would be advantageous to provide a natural sea shell massage implement with an adhesive holding the shell halves together that does not fail if exposed to multiple heating and cooling cycles that cause expansion and contraction of the shell.

SUMMARY

The exothermal therapeutic massage implements disclosed below satisfy these needs in the field of therapeutic massage. The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In one embodiment, an exothermic massage implement includes a heat conducting vessel having an inner chamber surrounded by a wall with an inner surface and an outer surface. A reactant is inside the inner chamber of the vessel. Combining the reactant with an activator causes an exothermic reaction that heats the wall and maintains the wall at a substantially constant elevated temperature for a duration of time. The reactant inside the inner chamber of the vessel may be a reactive powder mixture.

There may also be at least one aperture in the vessel wall, which may be covered by a cap engaged with the aperture, the cap having a valve that sequesters the combined reactant and activator inside the inner chamber of the vessel while allowing gas flow out of the inner chamber of the vessel.

The vessel containing the mixture in its inner chamber may be ceramic, plastic, metal, or made from natural materials such as stones or shells. The vessel may also be in the shape of a rolling pin with a hollow core. Alternatively, or additionally, other shapes which may have an ergonomic attribute or function, or aesthetic design may be used. The outer surface of the vessel wall may have portions with an abrasive texture and portions with a smooth texture.

The reactive powder mixture inside the inner chamber of the vessel may include sodium chloride particles or iron and activated charcoal particles, and the activator may be a fluid such as water or air. The powder mixture may be contained within a water-permeable pouch inside the inner chamber.

In another embodiment, an exothermic massage implement includes a heat conducting artificial stone having an inner chamber surrounded by a wall with an inner surface and an outer surface. A powder mixture is contained inside the inner chamber of the artificial stone. This powder mixture includes at least reactant particles. When the powder mixture is combined with an activator, an exothermic gel is created. This exothermic gel heats the artificial stone wall and maintains the artificial stone wall at a substantially constant elevated temperature for a duration of time.

Additionally, the outer surface of the wall may have portions with different radii of curvature and different textures, such that the user can use the same vessel for a variety of different modes of treatment.

In another embodiment, an exothermic therapeutic natural massage shell includes a natural bivalve shell comprising a first half and a second half adhered together with an adhesive to form a hollow chamber. An aperture is formed in the first half to provide a portal to the hollow chamber of the bivalve shell. A reactant is disposed inside the hollow chamber of the bivalve shell. Combining the reactant with an activator inside the hollow chamber of the bivalve shell causes an exothermic reaction that heats the bivalve shell and maintains the bivalve shell at a substantially constant elevated temperature for a duration of time. The adhesive adhering the first shell half to the second shell half includes a first elastomeric polymer bonding agent with balanced coefficient of expansion properties and a second flexible resin sealant that makes the adhesive moisture-proof.

In another embodiment, an exothermic therapeutic natural massage shell includes a natural bivalve shell comprising a first half and a second half adhered together with an adhesive to form a hollow chamber. An aperture is formed in the first half to provide a portal to the hollow chamber of the bivalve shell. A fluid-permeable pouch is disposed inside the hollow chamber of the bivalve shell. The fluid-permeable pouch contains a reactant such as a reactive powder mixture. Combining the reactant with an activator inside the hollow chamber of the bivalve shell causes an exothermic reaction that heats the bivalve shell and maintains the bivalve shell at a substantially constant elevated temperature for a duration of time. The fluid-permeable pouch may be a water-permeable non-woven polypropylene pouch or a paper-based pouch. The adhesive adhering the first half of the bivalve shell to the second half of the bivalve shell may include a first elastomeric polymer bonding agent with balanced coefficient of expansion properties and a second flexible resin sealant that makes the adhesive moisture-proof.

To the accomplishment of the foregoing and related ends, certain illustrative embodiments are described herein in connection with the following description and attached drawings. These embodiments are indicative, however, of but a few of the various ways in which the principles of the claimed subject matter may be employed and the claimed subject matter is intended to include all such embodiments and their equivalents. Other advantages and novel features may become apparent from the following detailed description when considered in conjunction with the drawings.

DETAILED DESCRIPTION

Figure 1:
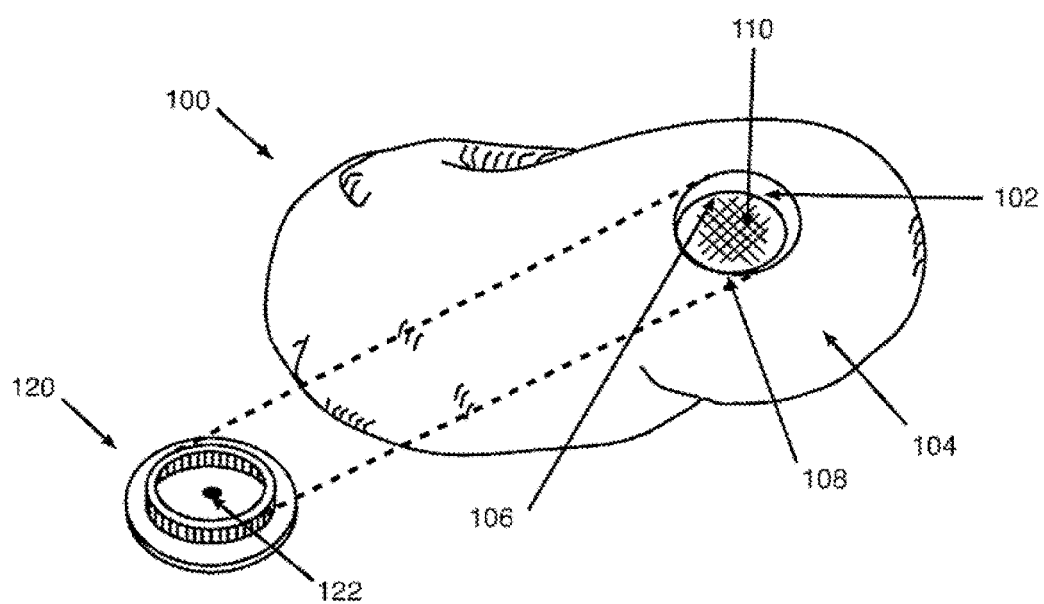
FIG. 1 is a perspective view of an exothermic massage implement.

The embodiments disclosed below address a need for massage implements that are maintained at a relatively constant elevated temperature for a significant duration of time, and for natural sea shell massage implements that are not damage by repeated heating and cooling cycles. In one embodiment, an exothermic massage implement includes a heat conducting vessel having an inner chamber surrounded by a wall with an inner surface and an outer surface. A reactant is inside the inner chamber of the vessel. Combining the reactant with an activator causes an exothermic reaction that heats the wall and maintains the wall at a substantially constant elevated temperature for a duration of time.

In another embodiment, an exothermic massage implement includes a heat conducting artificial stone having an inner chamber surrounded by a wall with an inner surface and an outer surface. A powder mixture is contained inside the inner chamber of the vessel. This powder mixture includes at least reactant particles. When the powder mixture is combined with an activator, an exothermic gel is created. This exothermic gel heats the wall and maintains the wall at a substantially constant elevated temperature for a duration of time.

In another embodiment an exothermic natural massage shell includes a natural bivalve shell comprising a first half and a second half adhered together with an adhesive to form a hollow chamber. An aperture is formed in the first half to provide a portal to the hollow chamber of the bivalve shell.

A reactant is disposed inside the hollow chamber of the bivalve shell. Combining the reactant with an activator inside the hollow chamber of the bivalve shell causes an exothermic reaction that heats the bivalve shell and maintains the bivalve shell at a substantially constant elevated temperature for a duration of time. The adhesive adhering the first shell half to the second shell half includes a first elastomeric polymer bonding agent with balanced coefficient of expansion properties and a second flexible resin sealant that makes the adhesive moisture-proof.

In various embodiments disclosed herein, the mechanism for heating is an exothermic composition that generates heat upon activation by a secondary, readily available activator. Examples of exothermic compositions that can be used may come from the combination of water with strong acids, combining alkalis and acids, polymerization, thermite reactions, aluminum-based reactions, magnesium-iron-based reactions, activated charcoal and iron-based reactions, anhydride reactions, and so forth. One particularly suitable, non-toxic exothermic composition is LAVA GEL® (manufactured by Forever Young International, Inc, Henderson, Nev., USA) which is known to exhibit a very controlled, regulated temperature for an extended period of time, with simply the addition of water or an electrolyte solution, such as saline water (as the activator). However, other exothermic compositions may be used, accordingly to design preference, including compositions that require activation or moderation by more than one activator or element.

By use of a non-electrical or non-fossil fuel heating source, the embodiments herein can be considered as self-contained units, portable, and also disposable with minimal to no environmental consequence. With a regulated, controlled exothermic reaction, overheating can be avoided, as well as burns that occur from such overheating. The embodiments can be of limited or of single use, whereby complications arising from reuse can be obviated. Also, with limited or single use products, they are of smaller size than institutional products. Therefore, the exemplary embodiments can also be easily shipped, easily stored (e.g., suitcase, handbag, etc.), and are much more affordable for the individual user.

An exothermic therapeutic massage implement is shown in FIG. 1. Massage implement 100 is a hollow vessel and includes inner chamber 110 which is surrounded by vessel wall 102. Vessel wall 102 has outer surface 104 and inner surface 106. Aperture 108 provides communication between inner chamber 110 and the ambient environment. Aperture 108 may be covered by cap or plug 120. Cap 120 includes valve 122, which is a small opening in cap 120. In some embodiments, massage implement 100 is aesthetically designed to resemble a natural stone.

Massage implement 100, whether or not designed to resemble a stone, may be manufactured in a wide variety of shapes. Massage implement 100 may have smoothly curved surfaces in multiple different contours so that the massage therapist can treat the massage recipient with different levels of pressure using the same implement 100. For example, massage implement 100 may have one side with a relatively small radius curved surface and another side with a larger radius curved surface. Pressing these different surfaces of massage implement 100 against the massage recipient's body will provide the massage recipient with different sensations.

Figure 2:
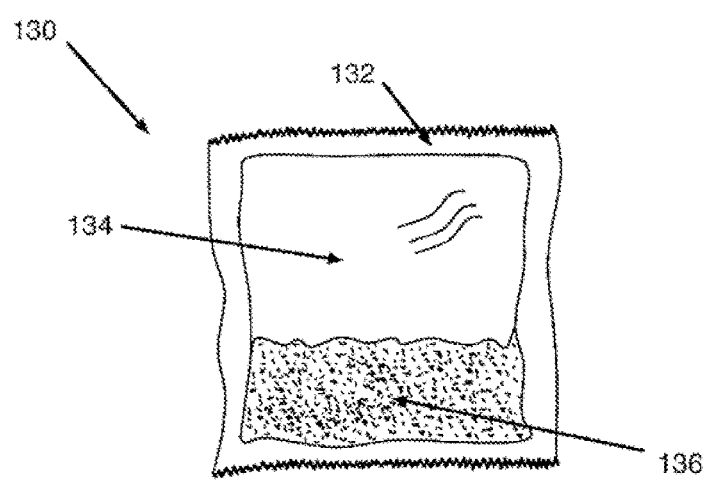
FIG. 2 is a front view of a pouch containing a powder mixture containing at least reactant particles.

FIG. 2 shows pouch 130 which is contained within the inner chamber or inserted through aperture 108 into inner chamber 110 of massage implement 100. Pouch 130 includes internal container 134 which is sealed about its periphery 132. Mixture 136 is contained inside internal container 134. Mixture 136 includes at least reactant particles. When the reactant particles are combined with an activator, an exothermic reaction occurs and heat is released. Pouch 130 is permeable to the activator that reacts with the reactant particles. The activator may be a liquid or gas. Where the activator is water or a water-based solution, pouch 130 is water permeable. The exothermic reaction is discussed in further detail elsewhere herein.

Figure 3:
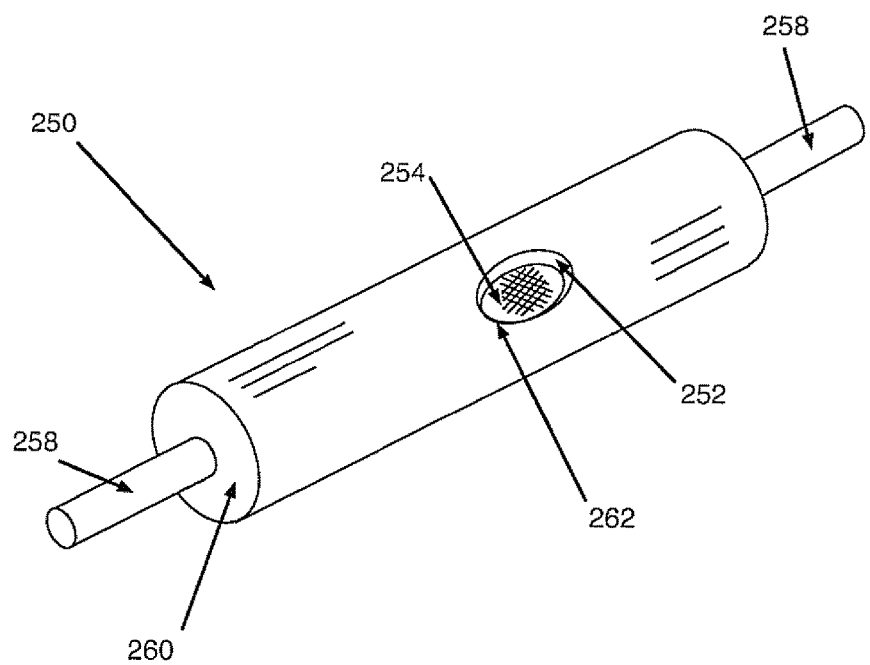
FIG. 3 is a perspective view of a rolling pin exothermic massage implement.
Figure 4:
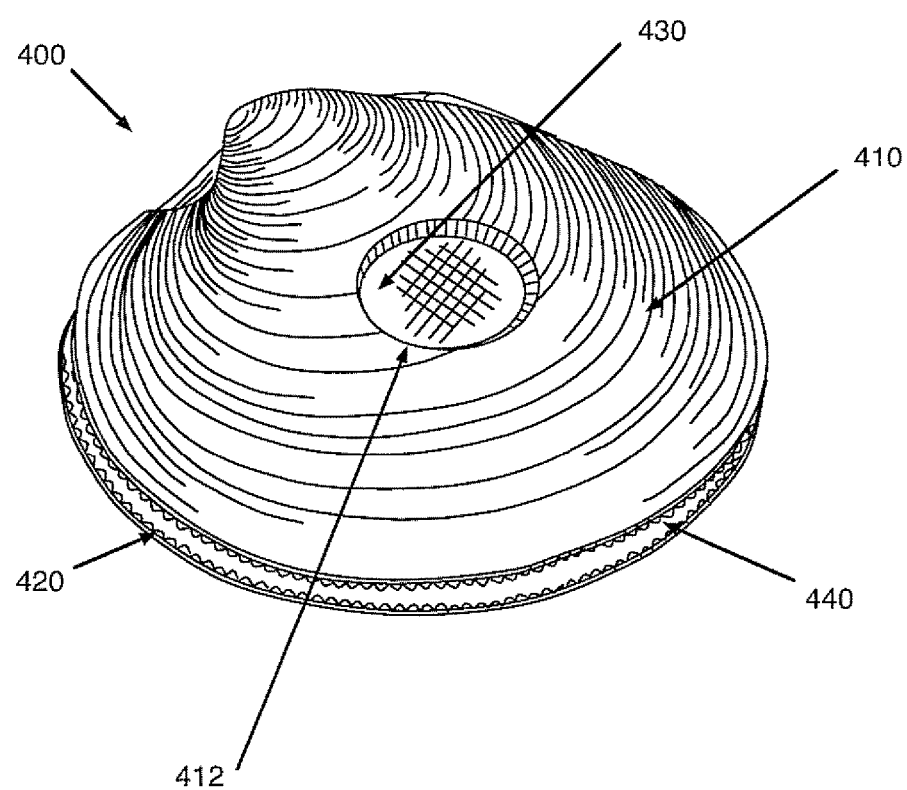
FIG. 4 is a perspective view of an exothermic therapeutic natural massage shell.

FIG. 3 shows an alternative embodiment of an exothermic therapeutic massage implement. Exothermic massage rolling pin 250 is a hollow vessel and includes inner chamber 254 surrounded by vessel wall 252. Vessel wall 252 is formed in the shape of a cylinder and includes flat end portions 260 at each end of the cylinder. Handles 258 are optionally attached to end portions 260. Handles 258 may be fixed relative to end portions 260, or end portions 260 and vessel wall 252 may be rotatable relative to handles 258. Vessel wall 252 or end portions 260 may incorporate an aperture, such as aperture 262 shown in FIG. 3. As with the previously disclosed embodiment, pouch 130 is contained inside inner chamber 254.

Regardless of the massage implement used, mixture 136 is placed inside its inner chamber, either directly, or inside pouch 130. Prior to use of the massage implement, the reactant particles are kept separate from the activator. Once the activator is added to the reactant particles inside the inner chamber of the massage implement, an exothermic reaction occurs and heat is released and transferred to the vessel walls, primarily by conduction. This exothermic reaction thus heats the massage implement to an elevated temperature, and the massage implement is maintained at approximately this temperature until the heat releasing phase of the exothermic reaction ceases.

Mixture 136 may also include salt particles. The salt particles may be sodium chloride, but other salts such as magnesium chloride may also be used. Alternatively, mixture 136 may include no salt particles, in which case the water combined with mixture 136 may contain dissolved salts. Although not illustrated, mixture 136 may also include perfume particles that give off pleasing aromas when combined with water.

To use exothermic therapeutic massage implement 100, a user places mixture 136 (which may be inside water-permeable pouch 130) into inner chamber 110 of massage implement 100. The user then adds a predetermined amount of activator to mixture 136 inside inner chamber 110 of massage implement 100. Where the massage implement has aperture 108 through which mixture 136 was inserted into inner chamber 110, activator is added to inner chamber 110 through aperture 108. After the activator is added, cap 120 is placed over aperture 108 so that mixture 136 (optionally inside pouch 130) cannot escape inner chamber 110, though gas can escape through valve 122 so as to prevent pressure buildup inside inner chamber 110.

The user then allows the exothermic reaction between the reactant particles and the activator to take place so that heat is transferred to vessel wall 102. Once massage implement 100 reaches the desired elevated temperature (which may be anywhere from 98.6° F. to as hot as the massage recipient desires, for example 115°-130° F.), the user applies massage implement 100 to the massage recipient. The user rubs massage implement 100 on the massage recipient's body using the technique of a typical hot stone massage. Unlike a conventional hot stone massage, however, massage implement 100 will remain at the relatively constant elevated temperature for a long duration of time, anywhere from 15 minutes to over 1 hour. If the user is using rolling pin massage implement 250 to perform the massage, the user will roll heated rolling pin massage implement 250 along the massage recipient's body.

Any of the massage implements disclosed above may be made from a wide variety of materials including ceramics, metals (such as stainless steel, copper, silver or gold), thermoplastic resins, glass, pottery and other moldable heat conducting materials, or natural materials such as natural stones and marble. The pouch containing the mixture likewise may be made from a wide variety of materials including woven and non-woven materials, paper, cellulose, natural fibers, polyethylene or polypropylene. The shape and size of the massage implements and pouch disclosed above may vary widely according to the design preferences of the user.

In another embodiment, an exothermic therapeutic massage implement is natural massage shell 400. Exothermic therapeutic natural massage shell 400 is a natural sea or freshwater shell, i.e. it was created by a living mollusk. Natural massage shell 400 includes first shell half 410 and second shell half 420 surrounding inner shell chamber 430. Although referred to as halves, it is to be understood that first shell half 410 and second shell half 420 are not necessarily exactly the same size, and first shell half 410 may be larger or smaller than second shell half 420. First shell half 410 and second shell half 420 are joined together along seal 440. First shell half 410 includes aperture 412 which allows for communication between inner shell chamber 430 and the ambient environment.

Similar to the previously disclosed embodiments, exothermic therapeutic natural massage shell 400 is used by placing a heat source such as exothermic pouch 130 inside inner shell chamber 430. Once the heat source is activated, for example by placing an activator such as water inside inner shell chamber where it combines with exothermic pouch 136, aperture 412 is closed with a cap such as cap 120. As explained above, cap 120 includes valve 122 which allows hot air and vapor to escape inner shell chamber 430 to prevent a dangerous buildup in internal pressure. Once heated, exothermic therapeutic natural massage shell 400 is used to provide massage therapy to a massage recipient. The shape of massage shell 400 is particularly well suited for massage therapy because its outer surface naturally has a wide range of curvatures, ranging from a very small radius curves adjacent seal 440 to large radius curves in the central portions of first and second shell halves 410 and 420.

It has been found that there are significant advantages to placing mixture 136 inside a pouch such as pouch 130, rather than placing mixture 136 directly inside the inner chamber of a massage implement such as natural massage shell 400. For example, if mixture 136 is placed directly inside the inner chamber, the user must clean out the inner chamber of the massage implement after every use. By placing mixture 136 inside pouch 130, the user can easily remove all of mixture 136 by simply pulling pouch 130 through the aperture leading to the inner chamber of the massage implement, such as aperture 412 in natural massage shell 400.

However, care must be taken in selecting an appropriate pouch material. The material must be permeable to the activator while still sequestering mixture 136 inside the pouch. For example, for water-activated reactants, the pouch must be water-permeable, and for air-activated reactants (such as activated charcoal and iron), the pouch must be air-permeable. It has been found that paper-based pouches (similar to teabags) satisfy the permeability requirement, but are not well-suited for use with water-activated reactants, particularly water-activated reactants that expand after being exposed to water. This is because the expanded paper-based pouch is easily damaged when being removed from the inner chamber of the massage implement through the aperture in the chamber wall. If the pouch is damaged and the mixture spills into the inner chamber of the massage implement, the purpose of using a pouch to contain the mixture is defeated.

For this reason it has been found that a synthetic non-woven polypropylene pouch is most suitable for use as pouch 130 containing mixture 136. A synthetic non-woven polypropylene pouch may be formed such that it is water and/or air permeable, yet is still strong enough to withstand being pulled through the aperture in the massage implement chamber wall, even if the pouch expanded after being exposed to an activator such as water. Although synthetic non-woven polypropylene has been found to be a particularly well-suited material, other materials satisfying the above requirements of permeability and durability are also contemplated.

In nature, the two halves of a bivalve shell are held together by the mollusk inside. However, after the shell is harvested and the inner chamber of the shell is thoroughly cleaned, the two halves of the shell are no longer physically held together. This presents a challenge when a shell is used an exothermic therapeutic massage implement because the shell slightly expands and contracts as it undergoes repetitive heating and cooling cycles. It has been found that standard adhesives such as epoxies are not suitable for adhering the two shell halves together because after several expansion/contraction cycles, the bond between the epoxy and the shells begins to break down and eventually fail. This is caused by the epoxy and the shell having substantially different coefficients of expansion so that the two materials expand different amounts when heated.

However, it is has been found that using an elastomeric polymer bonding agent sealed by a flexible moisture-proof resin sealant produces an adhesive with coefficient of expansion properties such that the shell-adhesive-shell bond does not deteriorate over repeated heating and cooling cycles. This is an important improvement over standard adhesives as it makes it possible to use natural shells as a massage implement that can be reused dozens of times without failure. One type of elastomeric polymer bonding agent found to be suitable is a mixture of talc powder, unsaturated polyester resin, polyester resin, titanium dioxide, styrene monomer, fumed silica and hollow glass microspheres with an organic peroxide catalyst, such as the putty sold under the trademark BONDO® (3M Company, St. Paul, Minn.). The flexible moisture proof resin sealant may be a two part polyester resin that prevents moisture from deteriorating the elastomeric bonding agent and the bond between the two shell halves.

It will be understood that many additional changes in the details, materials, steps and arrangement of parts, which have been herein described and illustrated to explain the nature of the invention, may be made by those skilled in the art within the principle and scope of the invention as expressed in the appended claims.

What is claimed is:

1. An exothermic natural massage shell, comprising:
a natural bivalve shell comprising a first half and a second half adhered together with an adhesive to form a hollow chamber;
an aperture formed in the first half to provide a portal to the hollow chamber of the bivalve shell;
an exothermic reactant disposed inside the hollow chamber of the bivalve shell, the reactant being removably inserted through the portal;
wherein the reactant is combined with an activator inside the hollow chamber of the bivalve shell which causes an exothermic reaction that heats the bivalve shell and maintains the bivalve shell at a substantially constant elevated temperature for a duration of time, the hollow chamber and the portal being reusable for repeated exothermic reactions wherein addition of water to the reactant inside the hollow chamber creates an exothermic gel that transfers heat to one or more walls of the halves of the natural bivalve shell; and
wherein the adhesive adhering the first half of the bivalve shell to the second half of the bivalve shell comprises a first elastomeric polymer bonding agent with coefficient of expansion properties operable to maintain first and second halves securely adhered through repeated heating and cooling cycles and a second flexible resin sealant that makes the adhesive moisture-proof.

2. The exothermic natural massage shell of claim 1, further comprising a cap engaged with the aperture formed in the first half, the cap having a valve that sequesters the reactant and activator inside the hollow chamber while allowing gas flow out of the hollow chamber.

3. The exothermic natural massage shell of claim 2, wherein heated air or vapor produced by the exothermic reaction escapes through the valve.

4. The exothermic natural massage shell of claim 1, wherein the reactant is contained within a water-permeable pouch inside the hollow chamber.

5. The exothermic natural massage shell of claim 1, wherein at least a portion of an outer surface of the bivalve shell has an abrasive texture.

6. The exothermic natural massage shell of claim 1, wherein at least a portion of an outer surface of one or more walls of the natural bivalve shell has a smooth texture.

7. The exothermic natural massage shell of claim 1, wherein an outer surface of the bivalve shell includes at least two portions, each with a different radius of curvature.

8. The exothermic natural massage shell of claim 1, wherein the outer surface of the bivalve shell includes at least two portions, each with a different texture.

9. The exothermic natural massage shell of claim 1, further comprising a cap detachably engaged with the aperture formed in the first half.

10. The exothermic natural massage shell of claim 1, wherein the first and second halves are each formed with different curved surfaces and associated radii.

11. An exothermic natural massage shell, comprising:
a natural bivalve shell comprising a first half and a second half adhered together with an adhesive to form a hollow chamber;
an aperture formed in the first half to provide a portal to the hollow chamber of the bivalve shell;
a fluid-permeable pouch disposed inside the hollow chamber of the bivalve shell, the fluid-permeable pouch being removably inserted through the portal and containing a reactant;
wherein the reactant is combined with an activator inside the hollow chamber of the bivalve shell which causes an exothermic reaction that heats the bivalve shell and maintains the bivalve shell at a substantially constant elevated temperature for a duration of time, the hollow chamber and the portal being reusable for repeated exothermic reactions wherein addition of water to the reactant inside the hollow chamber creates an exothermic gel that transfers heat to one or more walls of the halves of the natural bivalve shell; and wherein the adhesive adhering the first half of the bivalve shell to the second half of the bivalve shell comprises a first elastomeric polymer bonding agent with coefficient of expansion properties operable to maintain first and second halves securely adhered through repeated heating and cooling cycles and a second flexible resin sealant that makes the adhesive moisture-proof.

12. The exothermic natural massage shell of claim 11, wherein the fluid-permeable pouch is a water-permeable non-woven polypropylene pouch.

13. The exothermic natural massage shell of claim 11, wherein the fluid-permeable pouch is a paper-based pouch.

14. The exothermic natural massage shell of claim 11, wherein the activator is a liquid solution, and wherein a mixture of the reactant and the activator is sequestered inside the fluid-permeable pouch.

* * * * *